US012808756B2

(12) United States Patent
Neyens et al.

(10) Patent No.: US 12,808,756 B2
(45) Date of Patent: Nov. 24, 2026

(54) SAMPLE CHAMBER FOR MOLTEN METAL

(71) Applicant: Heraeus Electro-Nite International N.V., Houthalen (BE)

(72) Inventors: Guido Neyens, Houthalen (BE); Frank Mingneau, Houthalen (BE)

(73) Assignee: HERAEUS ELECTRO-NITE INTERNATIONAL N.V., Houthalen (BE)

(*) Notice: Subject to any disclaimer, the term of this patent is extended or adjusted under 35 U.S.C. 154(b) by 214 days.

(21) Appl. No.: 18/729,413

(22) PCT Filed: Jan. 9, 2023

(86) PCT No.: PCT/EP2023/050261
§ 371 (c)(1),
(2) Date: Jul. 16, 2024

(87) PCT Pub. No.: WO2023/138925
PCT Pub. Date: Jul. 27, 2023

(65) Prior Publication Data

US 2025/0116576 A1 Apr. 10, 2025

(30) Foreign Application Priority Data

Jan. 21, 2022 (EP) .................................... 22152596

(51) Int. Cl.
*G01N 1/12* (2006.01)
*G01N 21/69* (2006.01)
*G01N 33/205* (2019.01)

(52) U.S. Cl.
CPC ............. *G01N 1/125* (2013.01); *G01N 21/69* (2013.01); *G01N 33/205* (2019.01); *G01N 2021/695* (2013.01)

(58) Field of Classification Search
CPC ...... G01N 1/125; G01N 21/69; G01N 33/205; G01N 2021/695
See application file for complete search history.

(56) References Cited

U.S. PATENT DOCUMENTS 3,646,816 A 3/1972 Richard et al.
4,211,117 A 7/1980 Curé
(Continued)

FOREIGN PATENT DOCUMENTS

CN 104132828 A 11/2014
CN 111163878 A 5/2020
(Continued)

OTHER PUBLICATIONS

Thomas Dulski, A manual for the chemical analysis of metals, ASTM E1009, Mar. 1, 1996.

*Primary Examiner* — Laura Martin Sweeney
*Assistant Examiner* — Anthony W Megna Fuentes
(74) *Attorney, Agent, or Firm* — Blank Rome LLP

(57) ABSTRACT

A sample chamber for taking samples from a molten metal bath. The chamber comprises a flat cover plate and a housing, wherein the flat cover plate and housing are assembled together to form a sample cavity. The housing comprises an immersion face and an opposing end face, a top face and a bottom face. The housing comprises a first opening in the immersion face, and a second opening in another face. The top face has at least one indentation, comprising a distribution segment, a ventilation segment and an analysis segment and wherein the analysis segment is bounded by an analysis plane AP. The distribution segment and the ventilation segment are in a direction from the top face to an opposite face of the housing and the maximum and the minimum cross-sectional area of the analysis segment do not deviate from each other by more than 20%.

14 Claims, 3 Drawing Sheets

A

B

(56) References Cited

U.S. PATENT DOCUMENTS

| | | | | |
|---|---|---|---|---|
| 4,401,389 | A | 8/1983 | Theuwis | |
| 5,415,052 | A | 5/1995 | Baerts | |
| 2018/0164192 | A1 * | 6/2018 | Beyens | G01N 1/125 |

FOREIGN PATENT DOCUMENTS

| | | | |
|---|---|---|---|
| EP | 3336511 | A1 | 6/2018 |
| EP | 3336512 | A1 | 6/2018 |
| EP | 3336513 | A1 | 6/2018 |
| EP | 3336514 | A1 | 6/2018 |
| EP | 3581913 | A1 | 12/2019 |
| EP | 3581914 | A1 | 12/2019 |
| TW | 201833530 | A | 9/2018 |

* cited by examiner

SAMPLE CHAMBER FOR MOLTEN METAL

CROSS REFERENCE TO RELATED APPLICATIONS

This application is a U.S. National Phase of International Application No. PCT/EP2023/050261, filed on Jan. 9, 2023, which claims the benefit of EP Application No. 22152596.7, filed on Jan. 21, 2022.

FIELD OF THE INVENTION

The invention relates to a sample chamber for taking samples from a molten metal bath, particularly from a molten steel bath. The invention further relates to a sampler, comprising the sample chamber according to the invention and a carrier tube adapted to accommodate at least parts of the sample chamber.

BACKGROUND OF THE INVENTION

During the processing of metals in their molten state, it is necessary to obtain a representative sample of the molten metal at various stages of the process, for example, for the analysis or evaluation of either the chemical composition or the metallographic structure of the sample. Different methods for analyzing molten metals during manufacturing and further processing are known in the art.

Historically, the composition of a solidified metal sample is often determined using arc spark-optical emission spectroscopy, spark-OES, equipment. Spark-OES systems are generally the most effective systems for determining the chemical composition of a metal sample and for controlling the processing of molten metals due to their rapid analysis times and inherent accuracy. Thus, spark-OES analysis is typically used during molten metal processes for controlling the progress of molten metal production.

Spark-OES involves exciting atoms of a target sample of which knowledge of the composition is desired and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined in accordance with a calibration curve, thereby showing the relationship between the spectral intensity ratio (i.e., absolute radiation power of an element/absolute radiation power of the base metal) and the concentration of the element in the standard sample.

The spectral light may be produced by irradiation with electromagnetic radiation, such as by a laser or x-rays, but is generally produced for spark-OES by a short spark produced by a spark generator incident upon the target of which knowledge of its elemental composition is desired. In this case, the target is the metal sample. Spark generators, their intensity and their pulse regime vary according to the specific spark-OES equipment. Irrespective of the spark energy input, the accuracy and reliability of such emission spectrometers has been known to be dependent on the accuracy and quality of the detector and optics used to receive the radiation emitted from the sample and the homogeneity of the metal sample itself.

Broadly speaking, the spark-OES analysis procedure begins with the conductive metal sample being positioned with its analysis surface face down on a predetermined region of the stage of the spark-OES instrument, namely an optical emission spectrometer. More particularly, the sample is positioned so as to span and close the analysis opening of the spectrometer and an anode nearly abuts the analysis surface of the sample. Once the desired positioning of the sample and proximity of the anode and analysis surface is achieved, a spark is discharged between the anode and the conductive metal sample which is electrically connected to the spectrometer stage. This connection is, in most cases, made by gravitational force in combination with a small load. The analysis opening on the optical emission spectrometer is typically around 12 mm wide. This distance avoids that a spark arcs between the anode and the instrument housing. The optical detector receives the emitted light from the excavated material of the sample surface. The spark chamber, formed in part by the space between the anode and the metal sample, is continuously purged with argon or other inert gas in order to avoid air ingress which would lead to erroneous analysis values.

In order to lay flat upon the analysis opening of the spectrometer, the metal sample cannot have any extensions and the analysis surface of the metal sample must be smooth. There can be no part of the sample or sample housing which will break the plane of the analysis surface. The sample must span the analysis opening of the spectrometer and be of sufficient flatness to facilitate inert gas purging of the spark chamber and present a contiguous sample surface toward the anode.

The procedures and processes to obtain a representative analysis of metals are well known in the art as described in In Dulski, T. R. A Manual for the Chemical Analysis of Metals, ASTM International, 1996.

Conventional sampling devices which provide a coupon or disc of solid metal for use in spectrographic analysis are known. The geometric shape and dimensions of the solidified metal coupons obtained by such sampling devices will sometimes be specific to the type of metal or metallographic need. A general category of samples that are obtained by immersion devices for spark-OES analysis are samples having a disc or oval shape and a diameter or long length of 28 to 40 mm. Most commonly, such samples have a diameter or long length of about 32 mm and a thickness of 4 to 12 mm. Some samplers, commonly known as lollipop samplers, may produce a differently shaped sample, ranging from round to oval or longer, according to the requirements of the user, but most samples still have a diameter or long length of about 32 mm. Other samplers, commonly known as dual thickness samplers, combine two thicknesses within the same sample.

Typical sampling devices designed to obtain samples of molten metal for analysis by spark-OES include a sample chamber or mold cavity configured to be filled with molten metal upon immersion of the sampling device into the molten metal bath. The molds which delineate the mold cavity or sampling chamber are typically either a two-part clam shell type arrangement or a ring covered on its upper and lower sides by flat plates. Once the sample of metal is solidified, the molds are discarded and the sample is cooled, transported to the laboratory, analysis surface is grinded, a further cooling step upon which the sample is transported to the spark-OES for analysis.

U.S. Pat. No. 3,646,816 A describes this type of expendable immersion sampler, in which both flat surfaces of a disc-like sample are formed by chill-plates to achieve more rapid freezing and a pair of smoother surfaces which require less clean-up prior to analysis. Other prior art patents, such as U.S. Pat. No. 4,211,117 A, relate to a similar concept, while U.S. Pat. Nos. 4,401,389 A and 5,415,052 A provide examples of this metallurgical sample being combined with other sensors, one of which could be a temperature measuring sensor.

Samples produced by conventional sampling devices have a diameter of about 32 mm in a direction parallel to the spectrometer opening and a thickness of 4 to 12 mm in a direction perpendicular to the spectrometer opening. It has been found that a solidified sample of conventional thicknesses requires surface grinding from 0.8 to 5 mm of the as-cast surface, in order to achieve an analysis surface which is free from metal and non-metallic segregation. Conventional samples can only achieve this surface state after preparation processes to produce a geometry that is typically at least 28 mm in diameter in a direction parallel to the spectrometer opening and has a thickness which is typically less than 12 mm in a direction perpendicular to the opening. This after-preparation geometry is often handled by pre-analysis preparation equipment that mechanically grinds the sample surface and is also convenient for handling by robotic manipulators which advance the sample from preparation through analysis and removal to await the next sample.

Eliminating the need for surface preparation shortens the analysis time and is economically favorable to the metal producer. Various solutions to this problem are described in EP 3336511 A1, EP 3336512 A1, EP 3336513 A1, EP 3336514 A1, EP 3581913 A1 and EP 3581914 A1. These documents relate to Direct Analysis (DA) samplers which are a type of molten metal immersion sampler, which produce DA samples. DA samples do not require any kind of surface preparation before being analyzed, and thus can result in significant economic benefit both in terms of the availability of timely chemistry results as well as laboratory time savings by utilizing the spark-OES analysis method.

The aforementioned prior art describes sample chamber geometries with different segments, allowing a homogeneous distribution of the molten metal sample and its rapid chilling. In particular, the sample chambers comprise two zones with different thicknesses which build the face which is later positioned on the spectrometer during analysis, i.e. the analysis surface of the resulting sample.

However, these sample chambers and the resulting DA samples obtained with the aforementioned prior art DA samplers still have shortcomings as poor fixation of the samples in the sample chamber, non-flat analysis surfaces and/or uncontrolled or partial filling. Due to the segmented analysis surface with a rather “thin” zone, the complete filling of the analysis surface is not given under all circumstances, for example for lower temperature applications. Such segments, which are not entirely filled, result in fractioned surfaces, which can cause complications in the following analysis. In particular, a sealing with the spectrometer is hindered and parts of the obtained sample may detach and contaminate the spectrometer. Furthermore, the machining of such samplers demands high precision and several process steps.

Therefore, the invention aims at providing an improved DA sample chamber, and hence an improvement in the quality of accordingly obtained DA samples. Furthermore, it was an object of the present invention to provide a sampler to be used with such a sample chamber.

SUMMARY OF THE INVENTION

The invention provides a sample chamber for taking samples from a molten metal bath, particularly a molten steel bath, comprising a flat cover plate and a housing,

- wherein the flat cover plate and the housing are configured to be assembled together along an analysis plane AP to form a sample cavity,
- wherein the housing comprises an immersion face and an opposing end face, a top face and a bottom face, the top face and the bottom face extending between the immersion face and the opposing end face,
- wherein the housing comprises a first opening in the immersion face, and a second opening in another face,
- wherein the top face has at least one indentation,
- wherein the indentation comprises a distribution segment, a ventilation segment and an analysis segment and wherein the analysis segment is bounded by the analysis plane AP,
- wherein the distribution segment, the analysis segment and the ventilation segment are in flow communication with each other and with the first and the second opening of the housing, characterized in that

- the distribution segment and the ventilation segment are arranged below the analysis segment in a direction from the top face to the bottom face,
- the maximum and the minimum cross-sectional area of the analysis segment perpendicular to a central longitudinal axis X of the housing do not deviate from each other by more than 20%.

Advantageously, the configuration of the sample cavity, in particular the restricted deviation in the cross-sectional area of the analysis segment along the length of the housing and the two adjacent segments fully positioned underneath this segment, allows to obtain a sample which fully fills the sample plane in the analysis zone. Thus, the sample will be suited optimally for analysis without the risk of detached parts which could enter the spectrometer or an insufficient sealing between sample and spectrometer. Furthermore, the formation of fluid lines which solidify in the analysis plane can be minimized, which further enhances the accuracy of the analysis. Additionally, the resulting analysis surface is very smooth, further improving obtainable data quality. The geometry of the OES spectrometers applied for the analysis of these kind of samples demands for precise distances between the sample plane and the optical components of the spectrometer; corrugated sample surfaces thus have a significant negative impact on the obtainable data.

An additional benefit of this sample chamber design is its mechanical stability and the ease of production. The configuration of the distribution segment and the ventilation segment allow a drilling of these segments; a milling as in previous designs can be omitted.

The invention relates to a sample chamber for taking samples from a molten metal bath for direct analysis (DA) by optical emission spectroscopy (OES).

As used herein, the term “molten metal bath” is used to describe a melt in a furnace, in particular in a vessel. An alternative term for “molten metal bath” known to a skilled person is “metal melt”. The molten metal of the molten metal bath is not particularly restricted. According to a preferred embodiment, the molten metal bath is a molten steel bath.

The temperature of metal melts differs and usually depends on the composition of the metal and the stage of the melting process. According to a preferred embodiment, the temperature of the molten metal bath is in the range of 1500-1800 °C and more preferably in the range of 1500-1700 °C.

The sample chamber comprises a flat cover plate and a housing, configured to be assembled together to form a sample cavity. In other words, the flat cover plate closes a hollow volume of the housing to form the sample cavity of the sample chamber. The sample cavity is configured to receive molten metal and is to be understood as the volume in which molten metal is introduced during sampling.

The flat cover plate and the housing are configured to be assembled together along an analysis plane AP. In other words, the analyzable surface of a resulting sample when the sample chamber is filled with molten metal will lie in the analysis plane AP.

A "flat" cover plate is to be understood as essentially flat, i.e. without indentations or depressions which would provide a hollow volume for the sample when the sample chamber is assembled. As the skilled person will understand, a flat cover plate can still comprise parts which can for example be necessary for assembly, as a rim, a protrusion or a recess.

The flat cover plate can or cannot be formed of the same material as the housing. For example, the flat cover plate may be formed of fused silica or a refractory ceramic material. Preferably, the flat cover plate is formed of the same material as the housing.

The housing is preferably formed of one or more materials which are good thermal and electrical conductors, such as, but not limited to, aluminum, copper and other metals having similar thermal and electrical conductivity properties. Preferably, the housing is made of aluminum.

The mass of the flat cover plate preferably accounts for 10 to 20% of the overall mass of the sample chamber.

The flat cover plate has a first side or face and an opposing second side or face. The flat cover plate preferably has a thickness between 1 mm and 5 mm extending from the first face to the second face. The first face of the flat cover plate is configured to face the housing, and more particularly the top face of the housing, in the assembled configuration of the sample chamber.

Preferably, the flat cover plate has approximately the same width and length as the housing. However, it will be understood that the flat cover plate is not limited to such dimensions and may have a width and length greater or less than that of the housing.

The sample chamber according to the present invention comprises a housing. The housing can also be referred to as sample chamber body. It is to be understood, that the housing is not flat as the flat cover plate but comprises a body with a certain height enclosing a hollow volume.

The housing comprises an immersion face and an opposing end face. It will be understood by those skilled in the art that the phrase "immersion face" refers to the face or side at the end of the housing which is first immersed into molten metal in an immersion direction during operation. The immersion face and the opposing end phase can be parallel to each other.

The housing also comprises a top face and a bottom face extending between the immersion face and the opposing end face. The top face can also be referred to as top side of the housing. The bottom face is to be understood as opposite to the top face. Preferably, the bottom face is parallel to the top face. It is to be understood, that the top face and the bottom face are not arranged parallel to the immersion face and/or the opposing end face. In other words, an axis perpendicular to the central longitudinal axis X of the housing intersecting with the immersion face or the opposing end face cannot be parallel with the immersion face and/or the opposing end face.

The top face can intersect with the immersion face at an angle between 90 to 140°, preferably, at an angle of 90°. In the latter case, the immersion face and the top face are arranged perpendicular.

The top face can intersect with the opposing end face at an angle between 90 to 140°, preferably, at an angle of 90°. In the latter case, the immersion face and the opposing end face are arranged perpendicular.

Preferably, the top face is an analysis face, meaning it is the geometric side of the housing which is configured to be positioned face down upon the stage of optical emission spectrograph during analysis.

Typically, the housing is formed as a cuboid. Such a housing can be machined from a single piece of material.

Preferably, the housing has a length between 30 and 70 mm. The housing can have a width between 20 and 70 mm. The length is to be understood as the length from the immersion face to the opposing end face and the width is to be understood perpendicular to the length.

Throughout this application, a length is defined as a dimension parallel to a central longitudinal axis X in direction from the immersion face to the opposing end face of the housing. A width is defined as a dimension perpendicular to the longitudinal axis X and parallel to the top face, i.e. the analysis plane AP. A depth or thickness is defined as a dimension perpendicular to the longitudinal axis X and perpendicular to the top face, i.e. in a direction from the top face to the bottom face of the housing. More particularly, a depth is measured from a point at the analysis plane AP to the bottom end or boundary of each of the segments which will be specified in the following. A cross-sectional area dimension as discussed herein is equivalent to a width dimension multiplied by a depth dimension.

The housing comprises a first opening in the immersion face, and a second opening in another face. The other face can be any other face of the housing expect for the top face. The sample cavity extends from the first opening to the second opening of the sample chamber. It is to be understood that the flow direction of the molten metal is in a direction from the immersion face to the other face when the sample chamber is utilized to take a sample from a molten metal.

Preferably, the assembled sample chamber comprises only two openings, i.e. the first and the second opening.

Preferably, the first opening is configured to receive an inflow conduit. An inflow conduit enables the flow of molten metal from a molten metal bath into the sample chamber, in particular into the sample cavity.

In preferred embodiments, the second opening is configured to receive a gas coupler. At the face of the housing comprising the second opening, a gas port can be provided, which is preferably wholly contained within the housing.

The first and second openings are spaced apart from the top face, i.e. are arranged and spaced apart from the analysis plane AP. Thus, a homogeneous analysis surface can be obtained for the samples.

The top face of the housing comprises an indentation, an indentation can also be referred to as a depression. In other words, a portion of the top face is hollowed out. It is to be understood, that the indentation of the top face forms at least a part of a hollow volume of the housing, which comprises different segments. These segments collectively form the sample cavity. In particular, the indentation comprises a distribution segment, an analysis segment and a ventilation segment. In other words, the housing encloses a hollow volume which is structured in at least three segments. The distribution segment, the analysis segment and the ventilation segment are sequentially arranged in direct flow communication in the flow direction of the molten metal. The hollow volume of the housing can comprise additional segments which are not part of the indentation in the top face.

The distribution segment and the ventilation segment are arranged below the analysis segment in a direction from the top face to the bottom face of the housing, in particular below a bottom plane BP of the analysis segment. In other words, the ventilation segment and the distribution segment are not connected to the top face. Thus, an ideal and complete filling of the sample chamber in the region of the analysis segment may be ensured.

Preferably, the top face comprises a single indentation.

In one embodiment, the length of the indentation is between 20 and 50 mm, preferably between 25 and 40 mm.

It is to be understood, that the surface area of the housing delineating the indentation forms the physical boundaries of the hollow parts of the housing underlying the plane of the top face, i.e. the analysis plane AP. This surface area will further be referred to as the hollowed face of the housing. The projection of the hollowed face parallel to the analysis plane AP typically comprises a plurality of regions in different distances to the plane of the top face.

The distribution segment is the first segment of the indentation in the flow direction of the molten metal during operation. In particular, the distribution segment is positioned downstream of the first opening. The distribution segment is not connected to the top face.

The volume of the distribution segment is on one side bounded by the analysis segment. It is to be understood, that there is no physical delineation between the analysis segment and the distribution segment. However, these are considered separate segments for the practice of the invention. The boundaries of the distribution segment are defined by a first part of the hollowed face on the bottom side and on the opposite side by a bottom plane BP of the analysis segment. The boundary on the opposite side is to be understood as an imaginary boundary along an extension to a second part of the hollowed face. It is to be understood, that the second part of the hollowed face is arranged in a smaller distance to the analysis plane than the first part of the hollowed face.

Preferably, a central axis of the distribution segment is arranged with an angle between 45 to 90° to the central longitudinal axis X.

The distribution segment is further bounded by side walls. In a preferred embodiment, one of the side walls of the distribution segment intersects with the second part of the hollowed face at an angle between 4° and 90°, preferably at an angle between 5° and 80°. It can be particularly preferred, that one of the side walls of the distribution segment intersects with the second part of the hollowed face at an angle of 60°.

The cross-sectional area of the distribution segment parallel to the analysis plane AP can have any geometry. However, it can be preferred that the cross-sectional area has a polygonal or circular shape. In particular, a cross-sectional area with a circular shape allows an easy and precise machining of the housing, since it can be produced by a drilling step.

The cross-sectional area of the distribution segment can widen in direction of the metal flow, i.e. the cross-sectional area of the distribution segment increases in the direction from the first opening to the analysis segment. The cross-sectional area of the distribution segment parallel to the longitudinal axis X can range from 8 to 20 mm$^2$, preferably from 10 to 15 mm$^2$.

The depth of the distribution segment can range from 1 to 8 mm, preferably from 2 to 6 mm.

The indentation of the top face of the housing furthermore comprises the analysis segment downstream of the distribution segment and in direct flow communication with the ventilation segment. Preferably, the analysis segment is arranged above the central longitudinal axis X of the housing.

The analysis segment is bounded by the analysis plane AP on the top side. In other words, the analysis segment is on one side bounded by the flat cover plate when the sample chamber is assembled and the sample cavity is closed.

It is to be understood, that the geometry of the analysis segment in the analysis plane AP is defined by the indentation formed in the top face of the housing, i.e. the contour of the analysis segment is defined by the contour of the indentation. The analysis segment thus has an open end at the top face and an opposing bottom plane BP. More particularly, the bottom plane BP of the analysis segment is partly defined by the second part of the hollowed face of the housing and partly by an imaginary extension of the second part of the hollowed face.

The maximum and the minimum cross-sectional area of the analysis segment perpendicular to the central longitudinal axis X of the housing do not deviate from each other by more than 20%. This configuration enables a complete filling of the analysis plane AP with the sampled molten metal during operation.

The cross-sectional area of the analysis segment is to be understood as the cross-sectional area perpendicular to the central longitudinal axis X of the housing and perpendicular to the analysis plane AP. In a preferred embodiment, the maximum and the minimum cross-sectional area of the analysis segment do not deviate from each other by more than 10%, more preferred by not more than 5%.

In a preferred embodiment, the cross-sectional area of the analysis segment does not decrease after 50% of the length of the analysis segment, more preferably, not after 70% of the length. The direction of the length in this context is to be understood as the direction from the distribution segment towards the ventilation segment.

It can be preferred, that the maximum and the minimum cross-sectional area of the analysis segment do not deviate from each other.

Preferably, the cross-sectional area of the analysis segment is between 2.5 and 10 times the cross-sectional area of the ventilation zone parallel to the analysis plane AP.

Preferably, the cross-sectional area of the analysis segment is between 5 and 30 mm$^2$, more preferred between 10 and 25 mm$^2$.

The analysis segment can have a maximum depth between 0.5 and 4 mm, preferably between 1 and 3 mm. It can be preferred, that the analysis segment has a uniform maximum depth. The “maximum depth” is to be understood as the central depth of the analysis segment.

The depth of the analysis segment can be uniform or taper towards the edges. In other words, the cross-sectional profile of the bottom plane BP of the analysis segment perpendicular to the longitudinal axis X can have any shape, i.e. can have a flat, triangular or concave shape.

Preferably, the width of the analysis segment is constant in the direction of the central longitudinal axis X of the housing. In particular, the analysis segment can have a width between 6 and 14 mm, preferably between 8 and 12 mm.

In a preferred embodiment, the analysis segment has a length between 20 and 50 mm, preferably between 25 to 35 mm.

The ventilation segment is the last segment of the indentation in the flow direction of the molten metal. It is in flow connection with the second opening. However, the housing can comprise further segments positioned between the ventilation segment and the second opening.

The volume of the ventilation segment is on one side bounded by the analysis segment. It is to be understood, that there is no physical delineation between the analysis segment and the ventilation segment. The boundary of the ventilation segment is on one side defined by the bottom plane BP of the analysis segment. This boundary is to be understood as an imaginary boundary along an extension to a second part of the hollowed face.

In some embodiments, the ventilation segment can further be bounded by a third part of the hollowed face on the bottom side. In such configurations, the third part of the hollowed face is arranged in a larger distance to the analysis plane than the second part of the hollowed face. It can be preferred, that the first and the second part of the hollowed face have the same distance to the analysis plane AP.

The ventilation segment is further bounded by side walls. The cross-sectional area of the distribution segment parallel to the analysis plane, i.e. the cross-sectional area surrounded by the side-walls, can have any geometry. However, it can be preferred that the cross-sectional area has a polygonal or circular shape. In particular, a cross-sectional area with a circular shape allows an easy and precise machining of the housing, since it can be produced in a drilling step.

Preferably, the central axis of the ventilation segment is arranged with an angle between 45 to 90° to the central longitudinal axis X. It is to be understood, that the ventilation segment is not connected to the top face, i.e. it is arranged under the analysis segment. This configuration of the ventilation segment in relation to the analysis segment was surprisingly found to significantly enhance the quality of the obtainable samples and the relating analysis result, minimizing trapped gas and voids in the analysis surface.

In certain embodiments, the central axis of the distribution segment and the central axis of the ventilation segment are arranged with an angle between 45 to 90° to the central longitudinal axis X, in preferred embodiments both central axes are arranged with an angle of 90° to the central longitudinal axis X.

The ventilation segment can have an elongated shape in the direction perpendicular to the top face.

Preferably, the ventilation segment is positioned in a distance smaller than 20% of the length of the analysis segment from the end of the analysis segment, more preferably in a distance smaller than 10%. This configuration allows a complete filling of the analysis segment before the molten metal sample solidifies. The end of the segment is to be understood as the side of the analysis segment which is more proximate to the opposing end face than to the immersion face, i.e. the side of the housing which is opposite to the immersion face.

The cross-sectional area of the ventilation segment can taper in direction of the metal flow, i.e. the cross-sectional area of the ventilation segment can decrease in the direction from the analysis segment to the second opening. The cross-sectional area of the ventilation segment parallel to the longitudinal axis X can range from 0.2 to 5.0 $mm^2$, preferably from 0.5 to 3.0 $mm^2$.

The depth of the ventilation segment can range from 1 to 8 mm, preferably from 2 to 6 mm.

Preferably, the cross-sectional area of the distribution segment parallel to the analysis plane AP is between 0.5 and 2 times the cross-sectional area of the analysis segment. If the cross-sectional area of the distribution segment is too small, the inflowing molten metal will not be deaccelerated enough to reduce turbulent flow, which will result in inhomogeneous filling of the analysis plane AP.

Preferably, the length of the analysis segment in the direction of the central longitudinal axis X of the housing is higher than the depth of the distribution segment and ventilation segment perpendicular to the central longitudinal axis X.

In a preferred embodiment, the width of the analysis segment is higher than the width of the ventilation segment, in particular at least 3-times higher than the width of the ventilation segment.

Preferably, the width of the analysis segment perpendicular to the central longitudinal axis X of the housing is higher than the length of the distribution segment and/or the length of the ventilation segment along the central longitudinal axis X.

The hollow volume of the housing can also comprise an inflow segment configured to receive the molten metal and/or an inflow conduit, positioned prior to the distribution segment in the flow direction of the molten metal and in direct flow communication with the first opening. It can be preferred, that the central axis of the distribution segment is arranged with an angle between 45 to 90° to a central axis of the inflow segment.

Preferably, the cross-sectional area of the inflow segment perpendicular to the central longitudinal axis X is dependent upon the cross-sectional area of the analysis segment perpendicular to the central longitudinal axis X and/or the cross sectional-area of the distribution segment parallel to the analysis plane AP. Preferably, the cross-sectional area of the inflow segment is between 0.5 and 2 times of a cross-sectional area of the analysis segment. In a preferred embodiment, the cross-sectional area of the inflow segment is between 0.2 and 0.7 times the largest cross-sectional area of the distribution segment and thus lowers the inlet velocity required for metal mixing. If the cross-sectional area of the inflow segment is too small, there is not enough deceleration of the inflowing molten metal to reduce turbulent flow, which will result in poor filling of the sample cavity.

The hollow volume of the housing can also comprise a coupler segment, positioned after the ventilation segment in the flow direction of the molten metal and in direct flow communication with the second opening. Preferably, the coupler segment is configured to receive a gas coupler. It can be preferred, that the central axis of the ventilation segment is arranged with an angle between 45 to 90° to a central axis of the coupler segment.

The top face of the housing can include a ridge protruding therefrom and surrounding the indentation. Preferably, the flat cover plate sits flush against the ridge of the housing along the top face when the sample chamber is assembled.

In a preferred embodiment, a sealing member is provided on the first face of the flat cover plate configured to be positioned between the housing and the flat cover plate in the assembled configuration of the sample chamber. Advantageously, the sealing member prevents dirt to stick to either the cover plate or the housing, which would contaminate the surface of a spectrometer and influence the ongoing analysis and even the following analyses.

The sealing member is preferably a gas-tight sealing member. More particularly, the sealing member can be a gasket. The gasket may be of any shape.

Preferably, the sealing member consist of an essentially non-contaminating material for the samples in the sample chamber. In one embodiment, the sealing member is formed of silicone or any similar polymer, paper or cardboard. It will be understood by those skilled in the art that the sealing member may be formed of any material which would provide a gas tight seal between the flat cover plate and the housing. It will be understood by those skilled in the art that the sealing member may alternatively be formed as an O-ring.

The sample chamber, in particular the flat cover plate and the housing, can be held together by closing means. Preferably the closing means is a clip or a clamp.

Advantageously, by using a clip or clamp for holding the sample chamber together, the two parts are hold together by compressional forces applied by the closing means and no glues or cements are being used for said closing.

In a preferred embodiment, the closing means is made from metal. However, it will be understood by those skilled in the art that the closing means may be made of another suitable material which is capable to withstand an immersion in hot metal and provides the requisite compressive force.

It can be preferred, that the housing comprises first coupling means and the closing means comprises second coupling means, wherein the first coupling means and the second coupling means are configured to interact with each other. The coupling means of the housing can be realized as at least one recess, preferably two recesses, in the housing. Preferably, the at least one recess is positioned in a face of the housing which is positioned perpendicular to the top face.

In a preferred embodiment, the closing means are configured to apply a force in a direction perpendicular to the longitudinal axis X of the housing.

It can be preferred, that the sample chamber comprises identification means. In particular, such identification means can comprise an indestructible marking or label, for example such identification means can be a bar code or a QR code.

Furthermore, the sample chamber can comprise an inflow conduit configured to be received by the first opening of the housing. The inflow conduit is preferably made of a quartz material, more preferably a fused quartz material. However, it will be understood that the inflow conduit may be made of any other suitable material, including, but not limited to, a ceramic material.

The sample chamber can also comprise a gas coupler, configured to be received by the second opening. Thus, the sample chamber can be purged with a gas flow.

The invention also relates to a sampler, comprising the sample chamber according to the invention and a carrier tube adapted to accommodate at least parts of the sample chamber.

The sampler can further comprise a measuring head adapted to accommodate at least parts of the sample chamber, supported on the carrier tube. A measuring head is to be understood as a part which accommodates parts to be immersed in a molten metal to obtain measurements and which will subsequently be removed. In other words, a measuring head provides a disposable platform for immersible parts.

In an embodiment, the sampler comprises a protection cap attached to the first end of the inflow conduit.

BRIEF DESCRIPTION OF THE DRAWINGS

The following schematic drawings show aspects of the invention for improving the understanding of the invention in connection with some exemplary illustrations, wherein

FIG. 1 shows a sampler 1 for taking samples from a molten metal bath. The sampler 1 is suitable for immersion in and sampling of molten metal. The shown sampler 1 comprises a measuring head 2 which can be made of resin bonded silica sand. The measuring head 2 is supported on a carrier tube 3 which can be a paper carrier tube. In use, a probe holder or lance (not shown) is preferably inserted into the interior volume of the carrier tube 3 to provide the mechanical action necessary to submerse the measuring head 2 below the surface of a bath of molten metal in the immersion direction I.

The measuring head 2 comprises the sample chamber 20 for collection and retrieval of a sample of molten metal. The sample chamber 20 as shown is composed of a housing 22 and a flat cover plate 23 as shown in more detail in FIG. 2 from a front view perspective.

Figure 1:
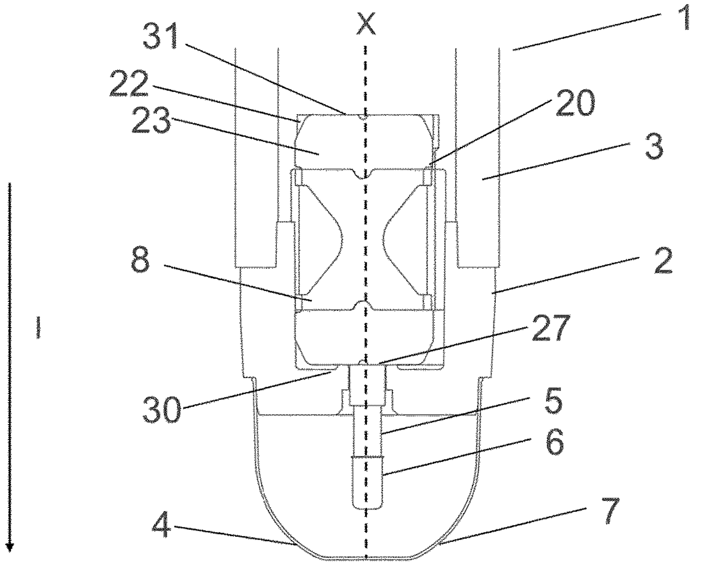
FIG. 1 shows a sampler for taking samples from a molten metal bath.

The measuring head 2 has a first end and an opposing second end. The first end of the measuring head 2 corresponds to an immersion end of the measuring head 4. The second end of the measuring head is configured to face a lance or probe holder. Also, the housing 22 of the sample chamber 20 has a first end 30 and an opposing second end 31. The first end of the housing 30 corresponds to an immersion face of the sample chamber 20. It will be understood by those skilled in the art that the phrase "immersion end" means the end of the assembly, respective the sampler, which is first immersed into molten metal. At the first end of the housing 30 an inflow conduit 5 is attached, which is received by a first opening 34. The inflow conduit 5 enables the flow of molten metal from the molten metal bath into the sample cavity 21 (not visible in the shown view of FIG. 1).

In use, the measuring head 2 is immersed in the immersion direction I into a hot metal bath. Thus, the inflow direction of the molten metal when introduced into the sample chamber 20 and its cavity 21 is in a direction opposite the immersion direction I parallel to the longitudinal axis X of the sample cavity 21.

The inflow conduit 5 is covered by a first protection cap 6. The first protection cap 6 is preferably made of metal, and more preferably steel. A second protection cap 7, in turn, covers (and more specifically encompasses) the first protection cap 6. The second protection cap 7 is attached to the measuring head 2. Preferably, the second protection cap 7 is made of metal, and more preferably steel.

The sample chamber 20 can be purged and pressurized by inert gas which is supplied via a coupler (not shown) connected to a second opening in the housing towards the inflow conduit 5. A skilled person will understand that the purging with inert gas is only necessary for certain applications. After the measuring head 2 is immersed below the surface of the hot metal bath, the second protection cap 7 melts due to the heat of the hot metal, thereby exposing the first protection cap 6 to the hot metal. Subsequently, the first protection cap 6 also melts, thereby placing the sample chamber 20 in fluid communication with the hot metal bath. Hot metal then enters the sample chamber, particularly via the first opening 34 from the immersion end 30 to the second end 31 while gas is exhausted out of the sample chamber cavity 21 through the second opening 35.

When the molten metal freezes in the sample cavity 21, the solidified metal sample is formed inseparably from the housing 22. The measuring head 2 is easily fractured allowing removal of the sampling chamber 20 from the carrier tube 3. If present, a clip 8 holding together the sample chamber 20 is removed. Unlike conventional sampling devices, the sample remains attached to the sample housing 22. Therefore, the term "sample", when referring herein to the metal coupon delivered to the OES, refers to the inseparable combination of the retrieved solidified sample and the sample housing 22.

Figure 2:
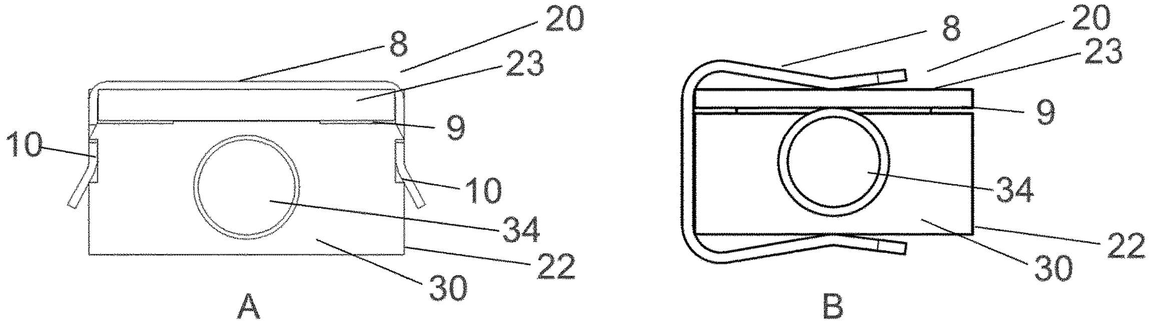
FIGS. 2A and 2B show alternative arrangements of the housing and the cover plate of the sample chamber held together by a clamp.

The housing 22 and the cover plate 23 of the sample chamber 20 can be held together by a clip or clamp 8, as also shown in FIGS. 2A and 2B, with a compression force sufficient to resist a tendency of the two parts to separate due to the force of molten metal flowing into and filling the sample cavity 21 and the force during the purging phase prior to the filling with the sample. The clip 8 can preferably be made from metal. FIGS. 2A and 2B show alternative front views of a sample chamber, i.e. the immersion face 30 and the first opening 34 of a housing 22. In the configuration illustrated in FIG. 2 A, a clip 8 is arranged mainly on the cover plate 23. The housing 22 comprises recesses 10 with which the clip can interact. The clip 8 can also be arranged sideways as shown in FIG. 2 B.

For practical purposes of assembly, the flat cover plate 23 can have approximately the same width and length as the housing 22. A first face of the cover plate 9 is configured to face the housing 22. A sealing member (now shown) can be provided on the first face of the cover plate 9 so as to be positioned between the housing 22 and cover plate 23 in the assembled configuration of the sample chamber 20

Figure 3:
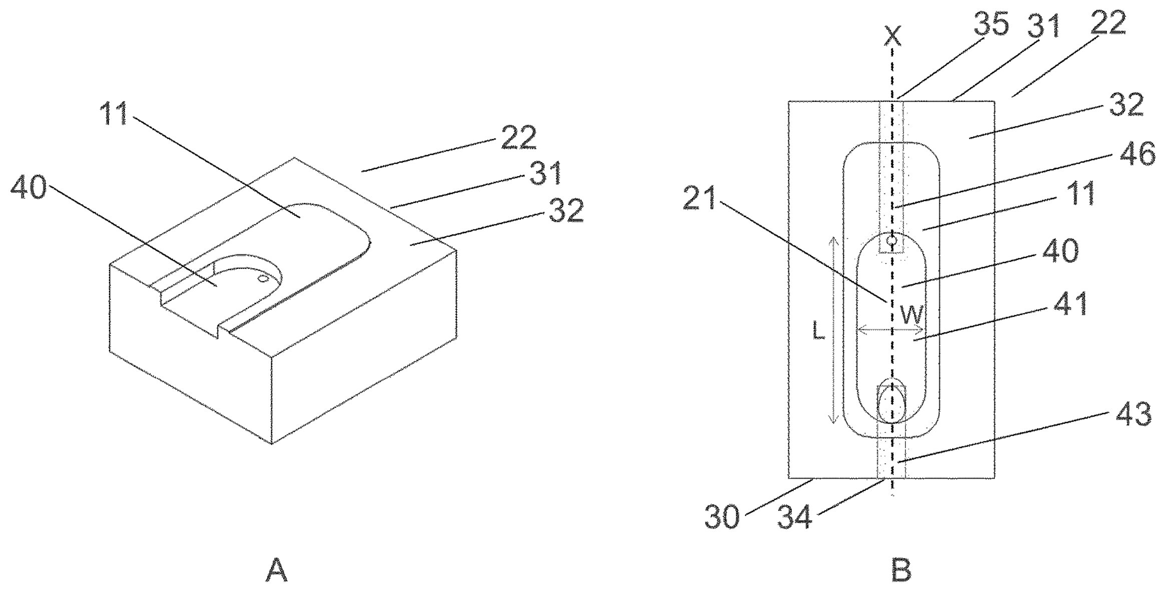
FIGS. 3A and 3B show different views of a housing.

FIGS. 3A and 3B show a housing 22 according to embodiments of the invention in different views. In particular, FIG. 3 A shows a cut through partial view, while FIG. 3 B shows a top view on the top face 32 of a housing 22 with the indentation 40. Segments positioned below the top face and thus not visible in the presented view are indicated by grey lines. The top face 32 shown in the figures is an analysis face, meaning it is the geometric side of the housing 22 in which the sample is collected, and which is thus configured to be positioned face down upon the stage of optical emission spectrometer during analysis. During analysis, inert gas is purged into the spark chamber of the spectrometer so that leaks between the sample to be analyzed and the spectrometer stage cannot be tolerated. Furthermore, the analysis surface of the solidified metal sample which abuts the cover plate helps to close the opening of the OES. A complete filling of this surface is therefore required to fully close the spectrometer opening. In particular, the front of the molten metal entering the sample cavity should at least reach the ventilation segment prior to freezing.

The top face 32 comprises the indentation 40 which forms at least a part of the sample cavity 21 of the sample chamber 20. As illustrated, the top face 32 extends between the immersion end or face 30 and the opposing end or face of the housing 31. FIGS. 3 A and B illustrate, that the top face 32 is hollowed out to form different segments of the sample cavity 21 for receiving the molten metal, the collection of molten metal sample and the ventilation of the cavity. The indentation 40 is defined by an elongated shape.

FIG. 3 B also illustrates where the longitudinal axis X of the housing and the width W and length L of the indentation 40 are to be found. Also visible is the hollowed face of the housing 41, comprising two more indentations below the plane of the top face. In the shown embodiment, the hollow part of the housing 22 comprises two additional segments, namely a distribution segment 43 and a coupler segment 46. It is to be noted, that both segments 43 and 46 are not visible in the portion of the housing shown in FIG. 3 A. As illustrated, the hollowed face 41 comprises all parts of the housing within the indentation 40 as visible in the shown view. In the illustrated embodiment, the opposing ends of the indentation 40 (i.e., the leading end and the trailing end in terms of the immersion direction I) are rounded for ease of machining. However, it will be understood by those skilled in the art, that the ends may have any shape. In the embodiment of the invention shown in FIGS. 3A and 3B, the top face of the housing 32 comprises a rim 11. Such a rim can enhance the sealing with the cover plate, especially in cases where an additional sealing element is also part of the sample chamber assembly.

Figure 4:
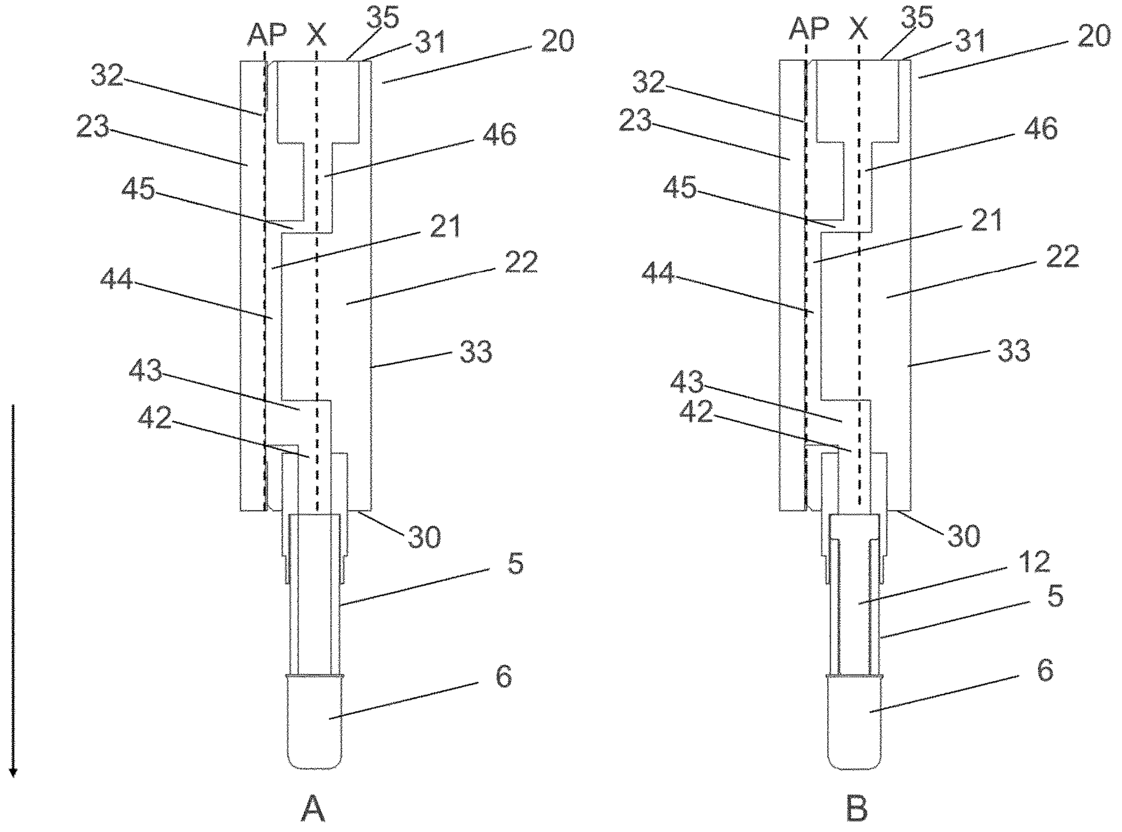
FIGS. 4A and 4B show side views of an assembled sample chamber.

FIGS. 4A and 4B show side views of an assembled sample chamber according to embodiments of the invention. In FIG. 4 A, the sample chamber 20 is shown in assembled configuration with an inflow conduit 5. The cover plate 23 is arranged on the top face 32 of the housing 22 along the analysis plane AP closing the hollow parts of the housing, thereby building the sample cavity 21. In the shown configuration, an inflow conduit 5 is in communication with an inflow segment 42 of the sample cavity 21. FIG. 4 B shows an alternative embodiment of the invention with a deoxidising element 12 arranged within the inflow conduit 5.

Figure 5:
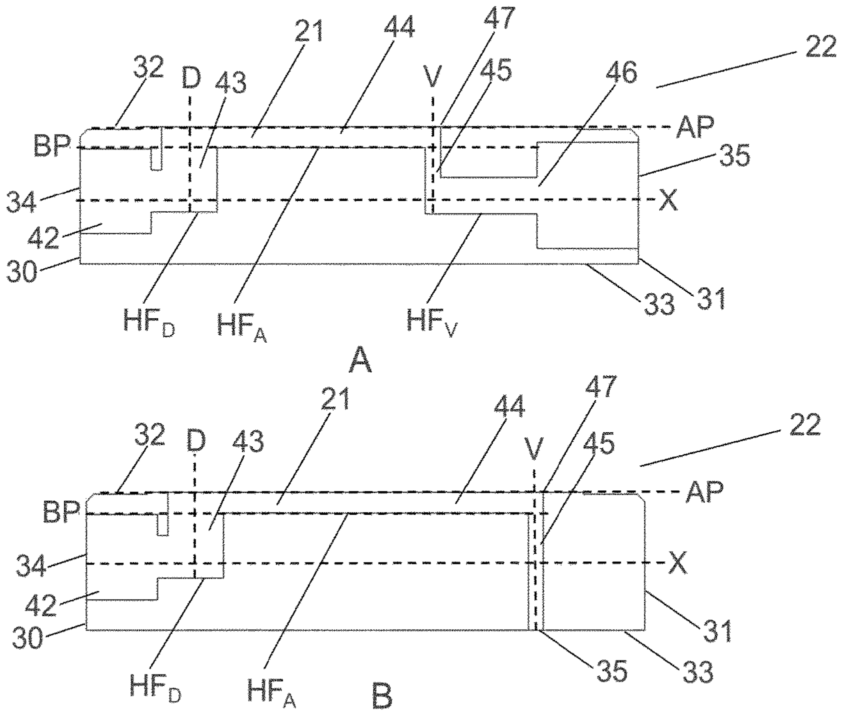
FIGS. 5A and 5B show different configurations of hollowed parts of the housing of the sample chamber in more detail.

FIGS. 5A and 5B show different configurations of the hollow volume, i.e. the sample cavity, of a housing 22 in more detail, illustrating the configurations of the different segments of the sample cavity 21 with respect to each other for certain embodiments. An upper part of the indentation confined by the analysis plane AP forms the analysis segment 44. The analysis segment 44 fully overlies a distribution segment 43 and a ventilation segment 45. The aforementioned three segments form a u-shaped indentation, which is in flow connection to the first opening 34, optional via an inflow segment 42. The analysis segment 44 as shown has a uniform depth in direction of the central longitudinal axis X. The ventilation segment 45 can further be connected to a coupler segment 46 positioned at the opposite side of the housing as illustrated in FIG. 5 A. In FIG. 5 B an alternative configuration is shown, in which the ventilation segment 45 is directly connected to a second opening 35 in the face of the housing opposite to the top face 32, i.e. the bottom face 33. In both embodiments, the ventilation segment 45 is positioned flush with the end of the analysis segment 47.

The analysis segment 44 is confined by the analysis plane AP on one side and a bottom plane BP on its opposite side, both planes are shown as dashed lines in FIGS. 5A and 5B. The bottom plane BP is partly an imaginary plane extending the plane of the hollowed face across the distribution segment 43 and the ventilation segment 45 along the central longitudinal axis X. The central axis of the distribution segment D as well as the central axis of the ventilation segment V are arranged perpendicular to the central longitudinal axis X and the analysis plane AP in both embodiments shown.

The hollowed face of the housing 22 comprises several parts as also indicated in the figures. A first part $HF_D$ which forms the bottom boundary of the distribution segment 43, a second part $HF_A$ which forms the bottom boundary of the analysis segment 44, and a third part $HF_V$ which forms the bottom boundary of the ventilation segment 45. In the illustrated configuration in FIG. 5 B, the hollowed face only comprises two segments.

Preferably, when a sample is taken, the molten metal fully fills and freezes in the analysis segment 44 against the cover plate 23, in particular along the analysis plane AP. The shown configuration of the segments of the hollowed parts of the housing ensures that these requirements are fulfilled. The minimum deviation of the cross-section of the analysis segment along its length together with the positioning of the ventilation segment completely below this segment ensures the complete filling before the molten metal front entering the sample chamber begins to solidify.

Figure 6:
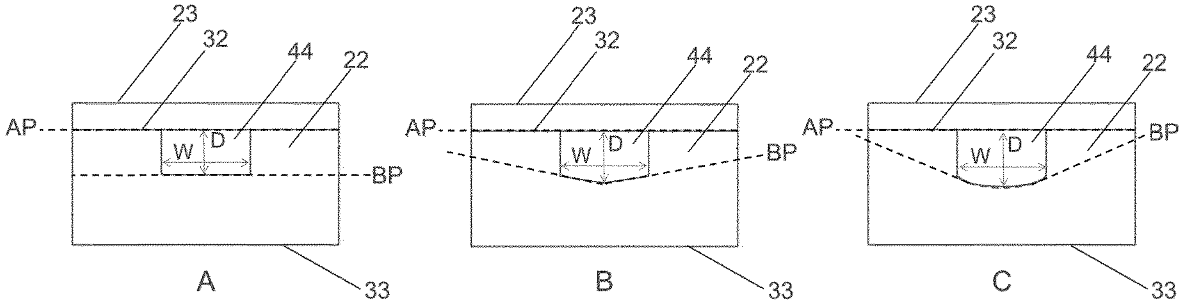
FIGS. 6A, 6B and 6C show the sample chamber with different possible cross-sectional geometries of the analysis segment in front views of the housing.

FIGS. 6A, 6B and 6C show embodiments of the sample chamber with different possible cross-sectional geometries of the analysis segment in front view of the housing 22 i.e. in the direction along the longitudinal axis X and the related parameters used to describe the analysis segment. Also shown is the cover plate 23. It is to be noted, that the shown dimensions are not necessarily drawn to scale. In FIG. 6 A, the cross-section of the analysis segment 44 has a rectangular shape. On the upper side, it is enclosed by the cover plate 23, which also defines the analysis plane AP. On the opposite side, the segment is bounded by the bottom plane BP. As a skilled person will understand, the cross-sectional area is determined by the width W and depth D of the segment. FIG. 6 B shows an analysis segment 44 with a triangular shaped bottom plane, whereas FIG. 6 C shows a convex shaped cross section of the analysis segment 44.

The features disclosed in the claims, the specification, and the drawings may be essential for different embodiments of the claimed invention, both separately or in any combination with each other.

REFERENCE SIGNS

1 Sampler
2 Measuring Head
3 Carrier Tube
4 Immersion End of Measuring Head
5 Inflow Conduit
6 First Protection Cap
7 Second Protection Cap
8 Clip
9 First Face of Cover Plate
10 Recesses
11 Rim
12 De-Oxidizing Element
20 Sample Chamber
21 Sample Cavity
22 Housing
23 Cover plate
30 Immersion End/Face of Housing
31 Opposing End/Face of Housing
32 Top Face of Housing
33 Bottom Face of Housing
34 First Opening of Housing
35 Second Opening of Housing
40 Indentation in Top Face
41 Hollowed Face
42 Inflow Segment
43 Distribution Segment
44 Analysis Segment
45 Ventilation Segment
46 Coupler Segment
47 End of Analysis Segment
I Immersion Direction
X Central Longitudinal Axis
AP Analysis Plane
D Central Axis of Distribution Segment
V Central axis of Ventilation Segment
$HF_D$ First Part of Hollowed Face
$HF_A$ Second Part of Hollowed Face
$HF_V$ Third Part of Hollowed Face

The invention claimed is:

1. A sample chamber for taking samples from a molten metal bath, comprising a flat cover plate and a housing, wherein the flat cover plate and the housing are configured to be assembled together along an analysis plane AP to form a sample cavity;

wherein the housing comprises an immersion face and an opposing end face, a top face and a bottom face, the top face and the bottom face extending between the immersion face and the opposing end face;

wherein the housing comprises a first opening in the immersion face, and a second opening in another face;

wherein the top face has at least one indentation, wherein the indentation comprises a distribution segment, a ventilation segment and an analysis segment and wherein the analysis segment is bounded by the analysis plane AP;

wherein the distribution segment, the analysis segment and the ventilation segment are in flow communication with each other and with the first and the second opening of the housing, wherein the distribution segment and the ventilation segment are arranged below the analysis segment in a direction from the top face to the bottom face and the ventilation segment and the distribution segment are not connected to the top face; and the maximum and the minimum cross-sectional area of the analysis segment perpendicular to a central longitudinal axis X of the housing do not deviate from each other by more than 20%.

2. The sample chamber according to claim 1, wherein a central axis of the distribution segment is arranged with an angle between 45 to 90° to the central longitudinal axis X of the housing.

3. The sample chamber according to claim 1, wherein a central axis of the ventilation segment is arranged with an angle between 45 to 90° to the central longitudinal axis X of the housing.

4. The sample chamber according to claim 1, wherein the cross-sectional area of the analysis segment does not decrease after 50% of the length of the analysis segment.

5. The sample chamber according to claim 1, wherein the maximum and the minimum cross-sectional area of the analysis segment do not deviate from each other.

6. The sample chamber according to claim 1, wherein the cross-sectional area of the analysis segment is between 2.5 and 10 times the cross-sectional area of the ventilation zone parallel to the analysis plane AP.

7. The sample chamber according to claim 1, wherein the width of the analysis segment is constant in the direction of the central longitudinal axis X of the housing.

8. The sample chamber according to claim 1, wherein the analysis segment has a length between 20 and 50 mm.

9. The sample chamber according to claim 1, wherein the ventilation segment is positioned in a distance smaller than 20% of the length of the analysis segment from the end of the analysis segment.

10. The sample chamber according to claim 1, wherein the width of the analysis segment is greater than the width of the ventilation segment.

11. The sample chamber according to claim 1, wherein the top face comprises a single indentation.

12. The sample chamber according to claim 1, wherein the assembled sample chamber comprises only two openings.

13. A sampler, comprising a sample chamber according to claim 1 and a carrier tube adapted to accommodate at least parts of the sample chamber.

14. The sample chamber according to claim 1, wherein the molten metal bath is a molten steel bath.

* * * * *